United States Patent [19]

Janick et al.

[11] Patent Number: Plant 6,268

[45] Date of Patent: Sep. 6, 1988

[54] APPLE TREE 'COOP 23'

[75] Inventors: Jules W. Janick, West Lafayette; Edwin B. Williams, Lafayette; Frank Emerson, West Lafayette, all of Ind.; Safi S. Korban; Daniel F. Dayton, both of Urbana, Ill.; Shawn A. Mehlenbacher, Hightstown, N.J.; L. Frederic Hough, Forest Falls, Calif.

[73] Assignee: Purdue Research Foundation, West Lafayette, Ind.

[21] Appl. No.: 856,152

[22] Filed: Apr. 25, 1986

[51] Int. Cl.[4] ..... A01H 5/00

[52] U.S. Cl. ..... Plt./34

[58] Field of Search ..... Plt. 34

*Primary Examiner*—James R. Feyrer

*Attorney, Agent, or Firm*—Barnes & Thornburg

[57] ABSTRACT

This invention relates to a new cultivar of apple tree which is characterized by resistance to apple scab and cedar apple rust, outstanding fresh fruit quality, smooth, slightly waxy skin, and a maturity approximately 7.5 to 8 weeks before 'Delicious' and 4 to 4.5 weeks before 'Prima.'

1 Drawing Sheet

BACKGROUND OF THE INVENTION

This invention is a new and distinct cultivar of apple tree. It was discovered by applicants in August, 1979, at West Lafayette, Ind., in the course of an attempt to develop improved apple trees with high fruit quality and resistance to *Venturia inaequalis* (Cke.) Wint., the causal agent for the apple scab disease. The tree is a seedling of known parentage planted in 1975 in Block F of the Hinsley Breeding Orchard at the Horticultural Farm of the Purdue University Agricultural Experiment Station, Lafayette, Ind. In the above orchard, its position was Row 20, Tree 42, having the description PRI 2845-1 in the breeding records.

The present new cultivar, which is designated as COOP 23, is a seedling produced from crossing the seedling PRI 1018-101 as the seed parent and the seedling N.J. 50 as the pollen parent in 1973 at Urbana, Ill. This new cultivar carries a genetic factor, $V_f$, inherited from *Malus floribunda* 821, causing it to be resistant to infection caused by *Venturia inaequalis*. The presence of this genetic factor has been repeatedly proven by controlled inoculation tests of the seedling in the Purdue greenhouse and by continuous field exposure to a natural population of the organism. The complete pedigree is shown below:

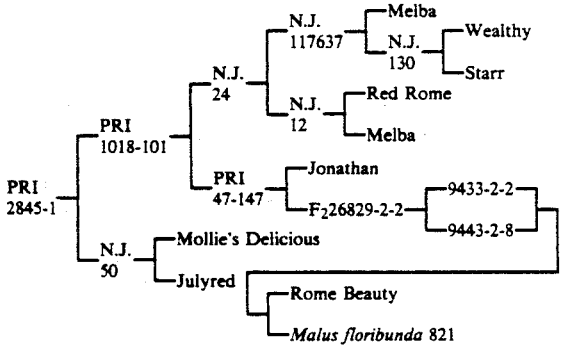

The new cultivar produces a vigorous, spreading tree with good annual crops borne on short spurs. It is field immune to apple scab caused by *Venturia inaequalis* (Cke.) Wint. and to cedar apple rust caused by *Gymnosporangium juniperi-virginianae* Schw. It is moderately resistant to powdery mildew caused by *Podosphaera leucotricha* (Ell. & Ev.) Salm. and to fireblight caused by *Erwinia amylovora* (Burr.) Winslow.

The tree flowers prior to 'McIntosh' and just prior to or at the same time as 'Redfree', which is described in U.S. Plant Pat. No. 4,322. The apple fruit has very good quality that is excellent for the season. The fruit holds texture and quality for at least four weeks during refrigerated storage at 34° F. When picked overripe, the fruit has a tendency to watercore.

After observation, the selection was asexually propagated by grafting on seedling apple roots and on three different apple dwarfing rootstocks. The grafted material has maintained the desired characteristics after propagation.

DESCRIPTION OF THE DRAWINGS

FIG. 1 is a photograph showing typical examples of fruit and foliage of the COOP 23 apple variety.

FIG. 1 shows a typical example of fruit and foliage of the COOP 23 cultivar. The following is a detailed description of the new cultivar in accordance with the Horticultural Colour Chart issued by the British Colour Council in collaboration with The Royal Horticultural Society.

FLOWER

Petals: 2 cm (0.8 inch) in length and 1.2 cm (0.5 inch) in width.

Corolla: 4 cm (1.6 inches) in diameter at anthesis.

Color: Crimson from Plate 22/3 to 22/2 (bud); fading to white (open flowers).

FRUIT

Shape: Oblate to round; uniform.

Size: Axial diameter 6.4 cm (2.5 inches); transverse diameter 7.4 cm (3.0 inches).

Color: Undercolor sap green (Plate 62/2); overcolor darkens to 90% ruby red (Plate 82/7); faint stripes on light side.

Skin: Smooth, slightly waxy, with moderately conspicuous round, depressed dots; medium thick and tough, no russeting.

Stem: Short, 1 to 1.5 cm (0.4 to 0.6 inch), thick, and clubbed.

Cavity: Acuminate, deep, medium to narrow in width, smooth to very slightly russeted.

Basin: Medium in depth, narrow in breadth with rounded sides; surface is irregular and wavy.

Calyx: Persistent, closed, and recurved.

Calyx tube: Conical.

Stamen remnants: Marginal.

Core lines: Clasping.

Carpels: Emarginate.

Seeds: Acuminate, not tufted.

Flesh:

*Texture.*—Medium to coarse, breaking, firm.

*Quality.*—Very good, excellent for season, mild subacid, rich flavor.

*Color.*—Naples yellow (Plate 403/3).

*Aroma.*—None to very faint.

Maturity season: 7.5 to 8 weeks before "Delicious."

Keeping quality: Retains quality and texture for at least 4 weeks in refrigerated storage at 34° F.

Use: Early maturity, summer dessert apple.

TREE

Tree: Spreading and vigorous, annual bearer.

Leaves: Ovate, serrate, margin apex is acuminate, rounded base, length to width ratio=1.8.

In particular, our new cultivar is distinguished on the basis of its resistance to apple scab, early maturity, dark solid red color, and outstanding dessert quality, which is unusual for an apple of its maturity.

We claim:

1. A new and distinct apple tree substantially as shown and described, particularly characterized by resistance to apple scab and to cedar apple rust, outstanding fresh fruit quality, smooth slightly waxy skin, ability to maintain quality in storage, and maturity approximately 7.5 to 8 weeks before 'Delicious' and 4 to 4.5 weeks before 'Prima.'

* * * * *

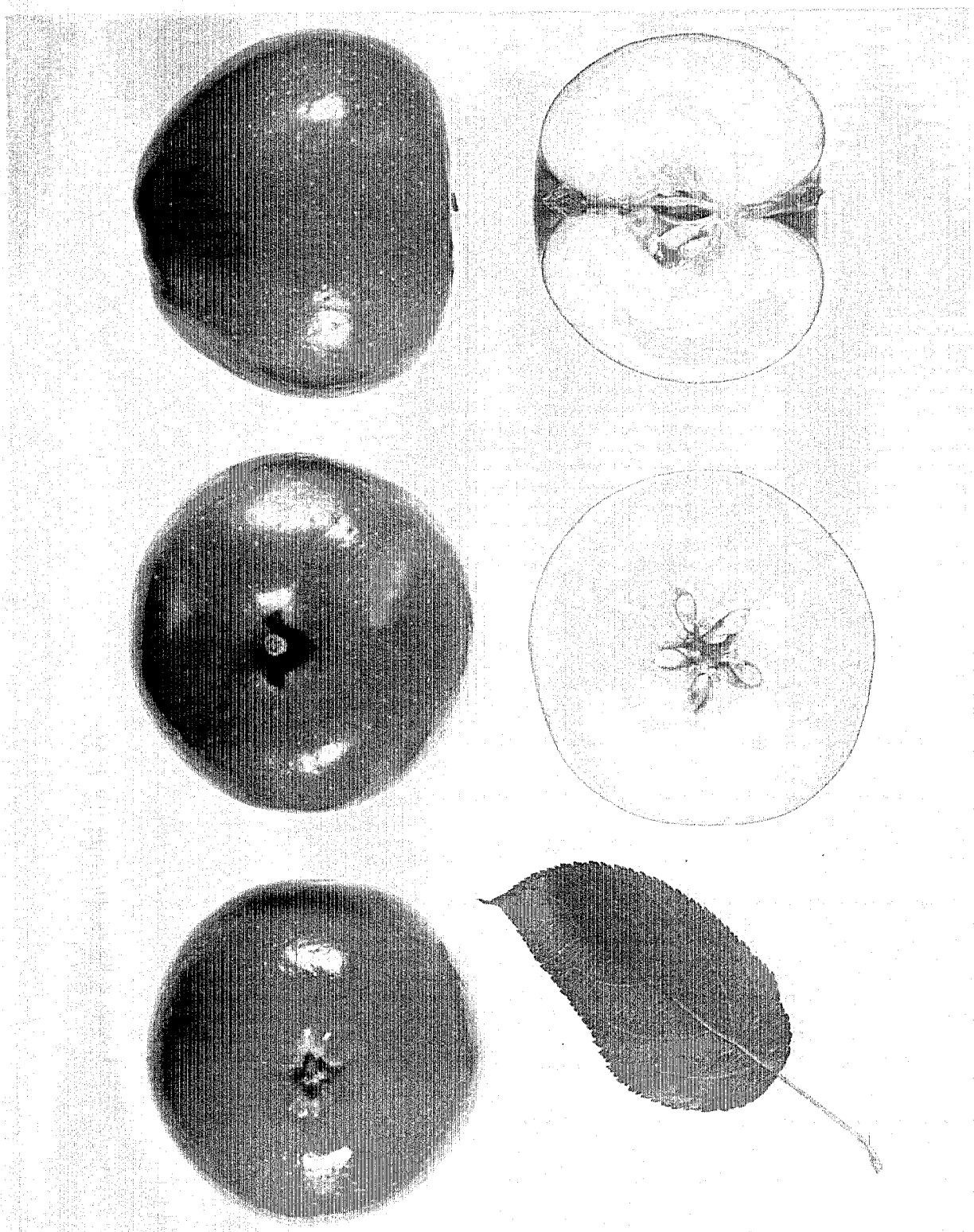

UNITED STATES PATENT AND TRADEMARK OFFICE

CERTIFICATE OF CORRECTION

PATENT NO. : Plant 6,268

DATED : September 6, 1988

INVENTOR(S) : Jules W. Janick et al.

It is certified that error appears in the above-identified patent and that said Letters Patent is hereby corrected as shown below:

On the bibliography page in the diagram showing the complete pedigree, please delete "9443-2-8" and insert therefor --9433-2-8--.

Signed and Sealed this

Twenty-eighth Day of February, 1989

*Attest:*

DONALD J. QUIGG

*Attesting Officer*

*Commissioner of Patents and Trademarks*